United States Patent
Nishimoto et al.

(10) Patent No.: US 8,682,414 B2
(45) Date of Patent: Mar. 25, 2014

(54) RADIATION THERAPY APPARATUS CONTROL METHOD AND RADIATION THERAPY APPARATUS CONTROLLER

(75) Inventors: Shigeru Nishimoto, Tokyo (JP); Takanobu Handa, Tokyo (JP); Kunio Takahashi, Tokyo (JP); Masahiro Yamada, Tokyo (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 346 days.

(21) Appl. No.: 12/811,125

(22) PCT Filed: Nov. 27, 2009

(86) PCT No.: PCT/JP2009/070012
§ 371 (c)(1),
(2), (4) Date: Aug. 26, 2010

(87) PCT Pub. No.: WO2011/064875
PCT Pub. Date: Jun. 3, 2011

(65) Prior Publication Data
US 2011/0196230 A1    Aug. 11, 2011

(51) Int. Cl.
*A61B 5/05*    (2006.01)

(52) U.S. Cl.
USPC ............ 600/425; 600/407; 600/427; 378/62; 382/128

(58) Field of Classification Search
USPC ............ 250/491; 315/500; 378/4, 10, 64, 65, 378/105, 197; 382/147; 600/426
See application file for complete search history.

(56) References Cited

U.S. PATENT DOCUMENTS

| | | | | |
|---|---|---|---|---|
| 6,307,914 B1 * | 10/2001 | Kunieda et al. | ................ | 378/65 |
| 7,436,928 B2 * | 10/2008 | Urano et al. | ................ | 378/65 |
| 2007/0211856 A1 * | 9/2007 | Urano et al. | ................ | 378/65 |
| 2007/0297566 A1 * | 12/2007 | Urano et al. | ................ | 378/65 |

FOREIGN PATENT DOCUMENTS

| | | |
|---|---|---|
| JP | 3673578 | 7/1997 |
| JP | 2001-505082 | 4/2001 |
| JP | 3785136 | 6/2004 |
| JP | 2006-051199 | 2/2006 |

(Continued)

OTHER PUBLICATIONS

Japanese Notice of Allowance mailed May 8, 2012 in corresponding Japanese Application No. 2010-525553 (including English translation).

*Primary Examiner* — Unsu Jung
*Assistant Examiner* — Serkan Akar
(74) *Attorney, Agent, or Firm* — Wenderoth, Lind & Ponack, L.L.P.

(57) ABSTRACT

A radiation control method includes: calculating degrees of similarity corresponding to matching target areas; calculating a specific image position where a specific image area corresponding to a maximum value of the degrees of similarity out of the matching target areas is positioned in a radiographic image; and calculating a drive amount with which a therapeutic radiation ray irradiation device is driven, based on the specific image position. Further, calculating one degree of similarity corresponding to one matching target region out of the degrees of similarity includes: referring to a template table in which the matching target areas are associated with sets of templates to calculate a set of templates corresponding to the one matching target area out of the sets of templates; and detecting, from the set of templates, a similar template most similar to a matching target image displayed in the one matching target area of the radiographic image.

12 Claims, 10 Drawing Sheets

(56) References Cited

FOREIGN PATENT DOCUMENTS

| JP | 2007-236729 | 9/2007 |
| JP | 2007-236730 | 9/2007 |
| JP | 2008-000456 | 1/2008 |
| JP | 4126318 | 1/2008 |

* cited by examiner

RADIATION THERAPY APPARATUS CONTROL METHOD AND RADIATION THERAPY APPARATUS CONTROLLER

TECHNICAL FIELD

The present invention relates to radiation therapy apparatus control methods and radiation therapy apparatus controllers, and more particularly to a radiation therapy apparatus control method and radiation therapy apparatus controller for use in radiation therapy (including particle-beam therapy) on a tumor-affected area within the human body.

BACKGROUND ART

Radiation therapy for treating a patient by irradiating a tumor-affected area with a therapeutic radiation ray is known in the art. A radiation therapy apparatus for performing radiation therapy includes an imager system that images a radiographic image of a patient, a therapeutic radiation ray irradiation device that irradiates the patient with a therapeutic radiation ray, and a driving device that drives the therapeutic radiation ray irradiation device. The radiation therapy apparatus calculates the position of the affected area of the patient based on the radiographic image and controls the driving device based on the calculated position so that the affected area is irradiated with the therapeutic radiation ray. That is, such radiation therapy apparatus allows irradiating the affected area with the therapeutic radiation ray even when the affected area moves in accordance with the respiration of the patient or the like.

Examples of such radiation therapy include stereoscopic moving-subject-tracking and surrogate moving-subject-tracking. The stereoscopic moving-subject-tracking is known in the art as disclosed in Japanese Patent Application Publication No. P2007-236729A, for example. The surrogate moving-subject-tracking is known in the art as disclosed in Japanese Patent Application Publication No. P2007-236730A, for example. In these types of radiation therapy, high therapeutic effect is desired, and therapeutic radiation rays are desired to cause a reduced dose for irradiation on normal cells, compared with that on cells of the affected area. Therefore, the radiation therapy apparatus is desired to irradiate the affected area with a therapeutic ray with higher accuracy and to calculate the position of the affected area with higher accuracy based on the radiographic image.

Japanese Patent Application Publication No. P2007-236729A discloses a radiation therapy apparatus controller for aligning a predetermined position of a target subject with a predetermined position of a radiation therapy apparatus with higher accuracy. The radiation therapy apparatus controller includes a therapeutic radiation ray irradiation device that emits a therapeutic radiation ray, an imager that generates an imager image of the target subject with a radiation ray passing through the target subject, and a driving device that moves a couch on which the target subject is placed with respect to the therapeutic radiation ray irradiation device. The radiation therapy apparatus controller includes a reference image generating part that collects reference imager images imaged by the imager, a radiographic image imaging part that images an imaged imager image of the target subject by the imager, and an affected area position control part that determines whether a relative position of the couch with respect to the therapeutic radiation ray irradiation device based on the position where a feature point included in the target subject is imaged in the imaged imager image and the position where the feature point is imaged in the reference imager image.

Japanese Patent Application Publication No. P2007-236730A discloses a radiation therapy apparatus controller which irradiates a part of a moving target subject with a radiation ray with an improved reliably. The radiation therapy apparatus controller includes a therapeutic radiation ray irradiation device that irradiates a part of the target subject with a therapeutic radiation ray, a motion detecting device that detects a motion of the target subject, and a driving device that moves the therapeutic radiation ray irradiation device with respect to the target subject. The radiation therapy apparatus controller includes an affected-area position database in which a set of motions are associated with a set of positions, a motion obtaining part that obtains the motion from the motion detecting device, and an irradiation position control part that moves the therapeutic radiation ray irradiation device by using the driving device so that the position associated with the motion out of the set of the positions is irradiated with the therapeutic radiation ray.

Japanese Patent Gazette No. 3,673,578 discloses a correlation-based tracking system configured to make a search in a search block provided around a reference block for a position with the highest degree of matching out of a plurality of templates of the reference block, to output data and instructions associated with the motion vector, and the matched template, and to stably achieve a tracking with high accuracy even if the shape of the subject is rapidly changed. The correlation-tracking system, which achieves tracking of the subject on the screen, includes means of setting a plurality of templates representing the changing shape and expression, including a rotation of the subject to predict the change thereof in advance, a reference block having the same size as the templates and a search block of a predetermined size around the reference block on the screen, means of sequentially matching the plurality of templates with shifts of the reference block in the search block to calculate the motion vector to the position where the degree of matching is highest, and tracking the subject while sequentially updating the position, and means that output data or instructions associated with the found template.

Japanese Patent Gazette No. 4,126,318 discloses a radiation therapy apparatus controller that detects a predetermined portion of the target subject with higher accuracy. The therapeutic apparatus controller controls a radiation therapy apparatus including a therapeutic radiation ray irradiation device that emits a therapeutic radiation ray and an imager that generates an imager image of the target subject by using a radiation ray passing through the target subject. The therapeutic apparatus controller includes a feature spot extracting part that generates a plurality of projection templates respectively representing the changes in the projection luminance in a case when a plurality of image templates are projected in one direction, which templates are different in the relation of the imaging positions of the target region of the target subject and the non-target region of the target subject, and generates a feature spot template representing a portion that is common among the plurality of projection templates; and an affected-area position calculating part that performs pattern matching on the change in projection luminance when the imager image is projected in one direction with the feature-spot template and calculates the position of the target region.

Japanese Patent Gazette No. 3,785,136 discloses a radiation therapy apparatus capable of facilitating treatment planning after radiation therapy is performed on a target subject. The radiation therapy apparatus includes a radiation-ray irradiation head that emits a therapeutic radiation ray, an image processing part that generates an image of an affected area of a target subject irradiated with the therapeutic radiation ray from the radiation-ray irradiation head, and a control part that controls the radiation-ray irradiation head and the image processing part so that cycles including generation of the image and irradiation of the therapeutic radiation ray are repeated, that the imaging of the image using the diagnostic X-ray in the second cycle following the first cycle is completed before the radiation of the therapeutic radiation ray in the first cycle, and that the processing of the imaged image during irradiation of the therapeutic radiation ray in the first cycle is completed to generate the image of the affected area.

Citation List

Patent Literatures
    Patent literature 1: Japanese Patent Application Publication No. P2007-236729A
    Patent literature 2: Japanese Patent Application Publication No. P2007-236730A
    Patent literature 3: Japanese Patent Gazette No. 3,673,578
    Patent literature 4: Japanese Patent Gazette No. 4,126,318
    Patent literature 5: Japanese Patent Gazette No. 3,785,136

SUMMARY OF INVENTION

An objective of the present invention is to provide a radiation therapy apparatus control method and radiation therapy apparatus controller which drive a therapeutic radiation ray irradiation device more accurately.

Another objective of the present invention is to provide a radiation therapy apparatus control method and radiation therapy apparatus controller which calculate a drive amount in driving a therapeutic radiation ray irradiation device, more quickly.

Still another objective of the present invention is to provide a radiation therapy apparatus control method and radiation therapy apparatus controller which calculate a drive amount in driving a therapeutic radiation ray irradiation device, more quickly, and drive the therapeutic radiation ray irradiation device, more accurately.

A radiation therapy apparatus control method according to the present invention includes: calculating a plurality of degrees of similarity corresponding to a plurality of matching target areas based on a radiographic image in which a target subject is imaged; calculating a specific image position where a specific image area corresponding to the maximum value of the plurality of degrees of similarity out of the plurality of matching target areas is positioned in the radiographic image; and calculating a drive amount with which the therapeutic radiation ray irradiation device that irradiates the target subject with a therapeutic radiation ray is driven based on the specific image position. Here, the operation of calculating one degree of similarity corresponding to one matching target region out of the plurality of degrees of similarity includes: referring to a template table in which the plurality of matching target areas are associated with a plurality of sets of templates to calculate a set of templates corresponding to the one matching target area out of the plurality of sets of templates; and detecting, from the set of templates, a similar template most similar to a matching target image displayed in the one matching target area of the radiographic image. The one degree of similarity indicates a degree of similarity with which the matching target image is similar to the similar template.

According to the above-described radiation therapy apparatus control method, the radiation therapy apparatus controller can calculate a plurality of degrees of similarity without matching all templates with each of the plurality of matching target areas, thereby calculating a specific image position at higher speed. Furthermore, according to the above-described radiation therapy apparatus control method, the radiation therapy apparatus controller matches some appropriate templates among all templates with each of the plurality of matching target areas, thereby calculating the specific image position more reliably and accurately. As a result, the radiation therapy apparatus controller can more accurately calculate a drive amount with which the therapeutic radiation ray irradiation device is driven at higher speed, and can more accurately drive the therapeutic radiation ray irradiation device at higher speed.

The radiation therapy apparatus control method according to the present invention preferably further includes: generating the template table based on all templates generated from a plurality of template generation radiographic images obtained at a plurality of different times by an imager imaging the radiographic image and a plurality of template positions where all the templates are displayed in the plurality of template generation radiographic images.

The plurality of template generation radiographic images are each divided into a first area and a second area with a straight line passing through one matching target position where the one matching target area is positioned in the radiographic image. The one set of templates includes a first template displayed in the first area out of all the templates and a second template displayed in the second area out of all the templates. The straight line is perpendicular to a straight line connecting a first template position and one matching target position. According to the above-described radiation therapy apparatus control method, a degree of similarity between the first template and the second template is relatively low, and these templates are more similar to the one matching target image. Therefore, the radiation therapy apparatus controller can use a template more similar to the one matching target image, compared with the case of using only templates placed in only one of the first area and the second area, can more accurately calculate the specific image position, and can more accurately drive the therapeutic radiation ray irradiation device.

The radiation therapy apparatus control method according to the present invention further includes calculating a specific-image movement range based on the plurality of template positions. Here, the plurality of matching target areas are areas included in the specific-image movement range out of all the matching target areas. According to the above-described radiation therapy apparatus control method, the radiation therapy apparatus controller can reduce the number of templates to be matched with one matching target area, can calculate the specific image position at higher speed, and can drive the therapeutic radiation ray irradiation device at higher speed.

The radiation therapy apparatus control method according to the present invention further includes calculating a three-dimensional specific-region movement range based on a plurality of other template generation radiographic images obtained by another imager different from the imager at a plurality of times and the plurality of template generation radiographic images. Here, the specific-image movement range is calculated based on the three-dimensional specific-region movement range. According to the above-described radiation therapy apparatus control method, the radiation therapy apparatus controller can more appropriately calculate the specific-image movement range, and can more appropriately reduce the number of templates to be matched with one matching target area.

The radiation therapy apparatus control method according to the present invention further includes calculating another specific image position based on another radiographic image obtained by another imager at the time when the radiographic image is imaged. Here, the drive amount is calculated further based on the other specific image position. According to the above-described radiation therapy apparatus control method, the radiation therapy apparatus controller can stereoscopically calculate the position where the specific region of the target subject is placed, can more appropriately calculate the drive amount, and can more appropriately drive the therapeutic radiation ray irradiation device.

The radiation therapy apparatus control method according to the present invention further includes calculating a predictive range based on a previous specific image position calculated based on a previous radiographic image obtained at a time previous to the time when the radiographic image is obtained. Here, the plurality of matching target areas are areas included in the predictive range among all the matching target areas that can be placed in the radiographic image. According to the above-described radiation therapy apparatus control method, the radiation therapy apparatus controller can reduce the number of templates for use in calculating one degree of similarity corresponding to one matching target area, can calculate the specific image position at higher speed, and can drive the therapeutic radiation ray irradiation device at higher speed.

A radiation therapy apparatus controller according to the present invention is provided with: a matching module that calculates a plurality of degrees of similarity corresponding to a plurality of matching target areas based on a radiographic image in which a target subject is imaged; a specific-image-position calculating module that calculates a specific image position where a specific image area corresponding to the maximum value of the plurality of degrees of similarity out of the plurality of matching target areas is placed in the radiographic image; and a radiation therapy module that controls a driving device that drives a therapeutic radiation ray irradiation device that irradiates the target subject with a therapeutic radiation ray based on the specific image position. When calculating one degree of similarity corresponding to one matching target region out of the plurality of degrees of similarity, the matching module refers to a template table in which the plurality of matching target areas are associated with a plurality of template sets and calculates a template set corresponding to the one matching target area out of the plurality of template sets, and determines, from the set of templates, a similar template most similar to a matching target image reflected on the one matching target area of the radiographic image. The one degree of similarity indicates a degree of similarity with which the matching target area is similar to the similar template.

The above-described radiation therapy apparatus controller can calculate a plurality of degrees of similarity without matching all templates with each of the plurality of matching target areas, thereby calculating a specific image position at higher speed. Furthermore, the above-described radiation therapy apparatus controller matches some appropriate templates out of all the templates with each of the plurality of matching target areas, thereby more reliably and more accurately calculating the specific image position. As a result, the radiation therapy apparatus controller can more accurately calculate a drive amount for driving the therapeutic radiation ray irradiation device at higher speed, and can more accurately drive the therapeutic radiation ray irradiation device at higher speed.

The radiation therapy module preferably controls the therapeutic radiation ray irradiation device so that the target subject is irradiated with the therapeutic radiation ray after the therapeutic radiation ray irradiation device is driven.

The radiation therapy apparatus controller according to the present invention preferably further includes a template table generating module that generates the template table based on all the templates generated from a plurality of template generation radiographic images obtained at a plurality of different times by an imager imaging the radiographic image and a plurality of template positions where all of the templates are imaged in the plurality of template generation radiographic images.

The plurality of template generation radiographic images are each divided into a first area and a second area with a straight line passing through one matching target position where the one matching target area is placed in the radiographic image. The one set of templates includes a first template displayed in the first area out of all of the templates and a second template displayed in the second area out of all of the templates. The straight line is perpendicular to a straight line connecting the first template position and one matching target position. Here, a degree of similarity between the first template and the second template is relatively low, and these templates are more similar to the one matching target image. Therefore, the radiation therapy apparatus controller can use a template more similar to the one matching target image, compared with the case of using only templates placed in only one of the first area and the second area, can more accurately calculate the specific image position, and can drive the therapeutic radiation ray irradiation device at higher speed.

The radiation therapy apparatus controller according to the present invention further includes a specific-image movement range calculating module that calculates a specific-image movement range based on the plurality of template positions. Here, the plurality of matching target areas are areas included in the specific-image movement range out of all the matching target areas. The above-described radiation therapy apparatus controller can reduce the number of templates to be matched with one matching target area, can calculate the specific image position at higher speed, and can drive the therapeutic radiation ray irradiation device at higher speed.

The specific-image movement range calculating module calculates a three-dimensional specific-region movement range based on a plurality of other template generation radiographic images obtained by another imager different from the imager at a plurality of times and the plurality of template generation radiographic images, and calculates the specific-image movement range based on the three-dimensional specific-region movement range. The above-described radiation therapy apparatus controller can more appropriately calculate the specific-image movement range, and can more appropriately reduce the number of templates to be matched with one matching target area.

The therapeutic module controls the driving device further based on another specific image position calculated based on another radiographic image obtained by another imager at the time when the radiographic image is imaged. The above-described radiation therapy apparatus controller can stereoscopically calculate a position where the specific region of the target subject is placed, and can more accurately irradiate the specific area with the therapeutic radiation ray.

The radiation therapy apparatus controller according to the present invention further includes a predictable-range calculating module that calculates a predictive range based on a previous specific image position calculated based on a previous radiographic image obtained at a time previous to the time when the radiographic image is obtained. Here, the plurality of matching target areas are areas included in the predictive range among all matching target areas that can be placed on the radiographic image. The above-described radiation therapy apparatus controller can reduce the number of templates for use in calculating one degree of similarity corresponding to one matching target area, can calculate the specific image position at higher speed, and can drive the therapeutic radiation ray irradiation device at higher speed.

When driving the therapeutic radiation ray irradiation device that irradiates the target subject with a therapeutic radiation ray, the radiation therapy apparatus control method and radiation therapy apparatus controller according to the present invention can more rapidly calculate a drive amount with which the therapeutic radiation ray irradiation device is driven, and can more accurately drive the therapeutic radiation ray irradiation device.

EMBODIMENTS OF INVENTION

Figure 1:
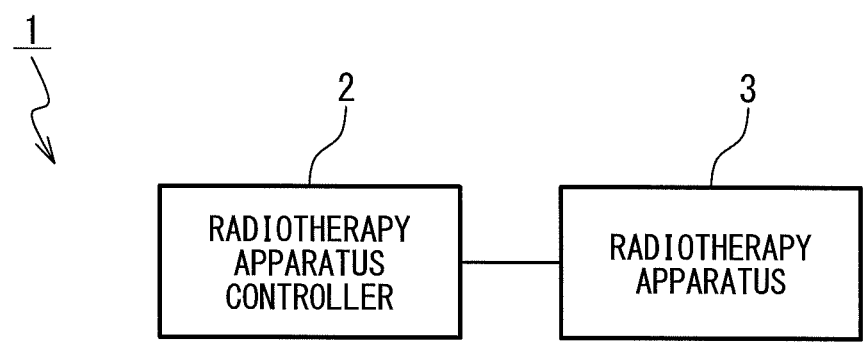
FIG. 1 is a block diagram depicting a radiation therapy system.

Referring to the drawings, embodiments of the radiation therapy apparatus controller according to the present invention are described. A radiation therapy apparatus controller 2 is applied to a radiation therapy system 1, as shown in FIG. 1. The radiation therapy system 1 includes a radiation therapy apparatus controller 2 and a radiation therapy apparatus 3. The radiation therapy apparatus controller 2 is a computer exemplified by a personal computer. The radiation therapy apparatus controller 2 and the radiation therapy apparatus 3 are connected to each other so as to bi-directionally transmit information.

Figure 2:
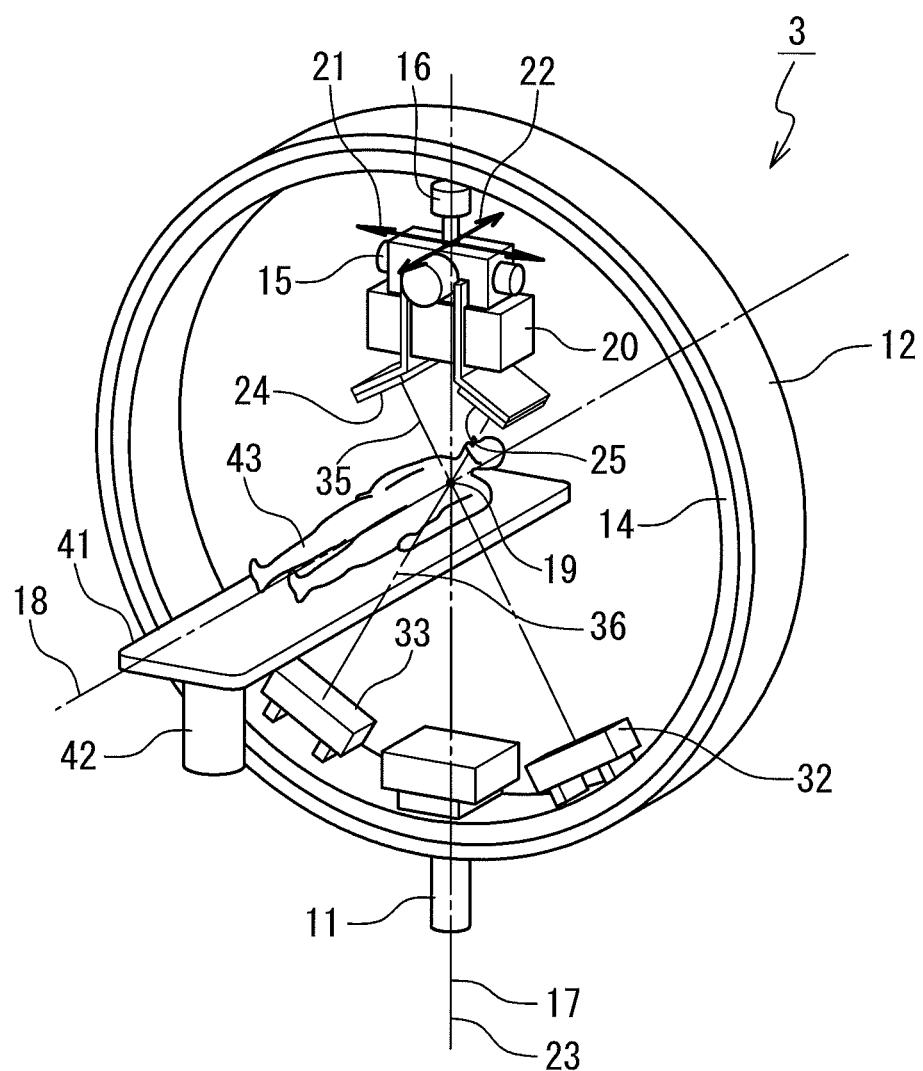
FIG. 2 is a perspective view of a radiation therapy apparatus.

FIG. 2 shows the radiation therapy apparatus 3. The radiation therapy apparatus 3 includes an O ring 12, a running gantry 14, and a therapeutic radiation ray irradiation device 16. The O ring 12 is formed in a ring shape, and supported on a base to be rotatable about a rotation axis 17. The rotation axis 17 is parallel to the vertical direction. The running gantry 14, which is formed in a ring shape, is placed inside the ring of the O ring 12 and supported on the O ring 12 to be rotatable about a rotation axis 18. The rotation axis 18 is perpendicular to the vertical direction, and passes through an isocenter 19 included in the rotation axis 17. The rotation axis 18 is fixed with respect to the O ring 12, that is, rotates around the rotation axis 17 together with the O ring 12.

The therapeutic radiation ray irradiation device 16 is placed inside the ring of the running gantry 14. The therapeutic radiation ray irradiation device 16 is supported on the running gantry 14 to be rotatable about a tilt axis 21 and about a pan axis 22. The pan axis 22 is fixed to the running gantry 14, and is parallel to the rotation axis 18 without crossing the rotation axis 18. The tilt axis 21 is orthogonal to the pan axis 22. The intersection point of the tilt axis 21 and the pan axis 22 is one meter away from the isocenter 19.

The radiation therapy apparatus 3 further includes a swivel drive device 11, a swing device 15, and a running drive device not shown. The swivel drive device 11 is controlled by the radiation therapy apparatus controller 2 to rotate the O ring 12 about the rotation axis 17. The swivel drive device 11 further measures the swivel angle at which the O ring 12 is placed with respect to the base, and outputs the swivel angle to the radiation therapy apparatus controller 2. The running drive device is controlled by the radiation therapy apparatus controller 2 to rotate the running gantry 14 about the rotation axis 18. The running drive device further measures the gantry angle at which the running gantry 14 is placed with respect to the O ring 12, and outputs the gantry angle to the radiation therapy apparatus controller 2. The swing device 15 is controlled by the radiation therapy apparatus controller 2 to rotate the therapeutic radiation ray irradiation device 16 about the pan axis 22 and rotate the therapeutic radiation ray irradiation device 16 about the tilt axis 21.

The therapeutic radiation ray irradiation device 16 is controlled by the radiation therapy apparatus controller 2 to emit a therapeutic radiation ray 23. The therapeutic radiation ray 23 is a cone beam with the intersection point where the pan axis 22 and the tilt axis 21 cross being taken as the vertex. The therapeutic radiation ray 23 is formed so as to have a uniform strength distribution. The therapeutic radiation ray irradiation device 16 includes a multi-leaf collimator 20. The multi-leaf collimator 20 is fixed to the therapeutic radiation ray irradiation device 16 so as to be placed in a region through which the therapeutic radiation ray 23 travels. The multi-leaf collimator 20 is controlled by the radiation therapy apparatus controller 2 to shield a part of the therapeutic radiation ray 23, and changes the shape of the irradiation field in irradiating a patient with the therapeutic radiation ray 23.

With the therapeutic radiation ray irradiation device 16 being supported on the running gantry 14 in this manner, the therapeutic radiation ray 23 always passes through or near the isocenter 19 when the therapeutic radiation ray irradiation device 16 is fixed to the running gantry 14 so as to be face the isocenter 19, even if the O ring 12 is rotated by the swivel drive device 11 or the running gantry 14 is rotated by the running drive device. That is, the therapeutic radiation ray 23 can be emitted in an arbitrary direction toward the isocenter 19 by running and swiveling.

The radiation therapy apparatus 3 further includes a plurality of imager systems. That is, the radiation therapy apparatus 3 includes a first diagnostic X-ray source 24, a second diagnostic X-ray source 25, a first sensor array 32, and a second sensor array 33. The first diagnostic X-ray source 24 is supported on the running gantry 14, and is placed inside a ring of the running gantry 14 so that the angle between the line segment connecting the isocenter 19 and the first diagnostic X-ray source 24 and the line segment connecting the isocenter 19 and the therapeutic radiation ray irradiation device 16 is an acute angle. The second diagnostic X-ray source 25 is supported on the running gantry 14, and is placed inside the ring of the running gantry 14 so that the angle between the line segment connecting the isocenter 19 and the second diagnostic X-ray source 25 and the line segment connecting the isocenter 19 and the therapeutic radiation ray irradiation device 16 is an acute angle. Furthermore, the second diagnostic X-ray source 25 is placed so that the angle between the line segment connecting the isocenter 19 and the first diagnostic X-ray source 24 and the line segment connecting the isocenter 19 and the second diagnostic X-ray source 25 is the right angle (90 degrees). The first sensor array 32 is supported on the running gantry 14, and is placed so as to oppose the first diagnostic X-ray source 24 across the isocenter 19. The second sensor array 33 is supported on the running gantry 14, and is placed so as to oppose the second diagnostic X-ray source 25 across the isocenter 19.

The first diagnostic X-ray source 24 is controlled by the radiation therapy apparatus controller 2 to emit a first diagnostic X-ray 35 toward the isocenter 19 at a predetermined timing. The first diagnostic X-ray 35 is a conical cone beam emitted from one point included in the first diagnostic X-ray source 24, the beam having the one point as a vertex. The second diagnostic X-ray source 25 is controlled by the radiation therapy apparatus controller 2 to emit a second diagnostic X-ray 36 toward the isocenter 19 at a predetermined timing. The second diagnostic X-ray 36 is a conical cone beam emitted from one point included in the second diagnostic X-ray source 25, the beam having the one point as a vertex.

The first sensor array 32 includes photo detectors. The first sensor array 32 is controlled by the radiation therapy apparatus controller 2 to generate a first radiographic image based on the X-ray received at the photo detectors. The second sensor array 33 includes photo detectors. The second sensor array 33 is controlled by the radiation therapy apparatus controller 2 to generate a second radiographic image based on the X-ray received at the photo detectors. These radiographic images are each formed of a plurality of pixels. The pixels are arranged in a matrix on the radiographic image, and each corresponds to a luminance. The radiographic image reflects the subject by the plurality of pixels being colored with the luminances corresponding to the plurality of pixels. Examples of the first sensor array 32 and the second sensor array 33 include an FPD (Flat Panel Detector) and an X-ray II (Image Intensifier).

The above-described imager system can generate a radiographic image with the isocenter 19 as a center on the basis of image signals obtained from the first sensor array 32 and the second sensor array 33.

The radiation therapy apparatus 3 further includes a couch 41 and a couch drive device 42. The couch 41 is supported on the base so as to be rotatable about the x-axis, the y-axis and the z-axis and so as to be able to make translational movements in parallel with the x-axis, y-axis, and z-axis. The x-axis, y-axis, and z-axis are orthogonal to each other. The couch 41 is used for a patient 43 to be treated by the radiation therapy system 1 to lie down thereon. The couch 41 includes a fixture not shown. The fixture fixes the patient 43 to the couch 41 to prevent the patient 43 from moving. The couch drive device 42 is controlled by the radiation therapy apparatus controller 2 to cause the couch 41 to make a rotational movement and cause a translational movement.

Figure 3:
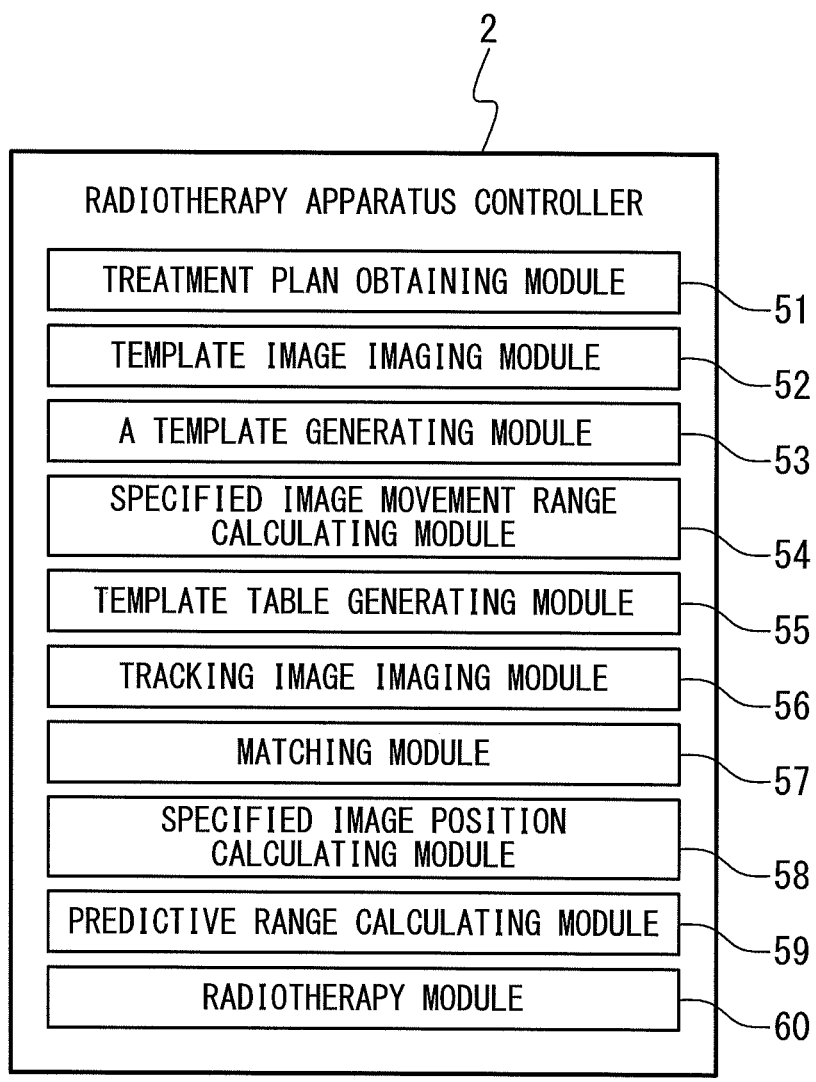
FIG. 3 is a block diagram of a radiation therapy apparatus controller.

FIG. 3 is a block diagram of the radiation therapy apparatus controller 2. The radiation therapy apparatus controller 2 is a computer, including a CPU, a storage device, a removable memory drive, a communication device, an input device, an output device, and an interface not shown. The CPU executes computer programs installed onto the radiation therapy apparatus controller 2 to control the storage device, the input device, and the output device. The storage device stores the computer programs, data used in the CPU, and data generated by the CPU. The removable memory drive is used to read data recorded on a recording medium when the recording media is inserted thereinto. In particular, the removable memory drive is used in an installation of a computer program onto the radiation therapy apparatus controller 2 when the recording medium having the computer program recorded thereon is inserted. The communication device downloads data distributed from another computer connected via a communication line network onto the radiation therapy apparatus controller 2. In particular, the communication device is used when downloading a computer program from another computer to the radiation therapy apparatus controller 2 and installing the computer program onto the radiation therapy apparatus controller 2. The input device outputs data generated with an operation by a user to the CPU. Examples of the input device include a keyboard and mouse. The output device outputs the information generated by the CPU in a user-recognizable manner. Examples of the output device include a display that displays an image generated by the CPU.

The interface outputs data generated by external devices connected to the radiation therapy apparatus controller 2 to the CPU, and outputs data generated by the CPU to the external devices. The external devices include the swivel drive device 11, the running drive device, the swing device 15, the therapeutic radiation ray irradiation device 16, the multi-leaf collimator 20, the first diagnostic X-ray source 24, the second diagnostic X-ray source 25, the first sensor array 32, the second sensor array 33, and the couch drive device 42.

The computer program installed onto the radiation therapy apparatus controller 2 is formed of a plurality of computer programs for the radiation therapy apparatus controller 2 to achieve each of the functions thereof. The functions include a treatment plan obtaining module 51, a template image imaging module 52, a template generating module 53, a specified image movement range calculating module 54, a template table generating module 55, a tracking image imaging module 56, a matching module 57, a specified image position calculating module 58, a predictive range calculating module 59, and a radiation therapy module 60.

The treatment plan obtaining module 51 obtains treatment plans from the input device. The treatment plans include three-dimensional data and indicate combinations of the irradiation angle and dose. The three-dimensional data are generated based on a plurality of radiographic images imaged by using a modality other than the radiation therapy apparatus 3. The three-dimensional data correlate a plurality of transmittances with a plurality of voxels. The plurality of voxels correspond to a plurality of rectangular parallelepipeds which tightly fill the space where the patient 43 is placed. An example of the rectangular parallelepiped is a cube with each side being 0.4 mm. The transmittance corresponding to each voxel represents an X-ray transmittance of the cube at the position corresponding to the voxel. The three-dimensional data indicate stereoscopic shapes of organs of the patient 43 lying down on the bed, and the positions where the organs are positioned. The organs include the affected area of the patient 43. The irradiation angle indicates a direction in which the affected area of the patient 43 is irradiated with the therapeutic radiation ray 23, indicating a couch position, an O-ring rotation angle, and a gantry rotation angle. The couch position indicates the position of the couch 41 with respect to the base. The O-ring rotation angle indicates the position of the O ring 12 with respect to the base. The gantry rotation angle indicates the position of the running gantry 14 with respect to the O ring 12. The dose indicates a dose of the therapeutic radiation ray 23 with which the patient 43 is irradiated at each irradiation angle.

The template image imaging module 52 controls the radiation therapy apparatus 3 to obtain a moving picture of the patient 43 lying down on the couch 41. That is, the template image imaging module 52 controls the couch drive device 42 so that the couch 41 is placed at the couch position with respect to the base. The template image imaging module 52 further controls the swivel drive device 11 so that the O ring 12 is placed at the O-ring rotation angle with respect to the base. The template image imaging module 52 further controls the running drive device of the radiation therapy apparatus 3 so that the running gantry 14 is placed at the gantry rotation angle. The template image imaging module 52 further controls the first diagnostic X-ray source 24 so that the patient 43 is cyclically irradiated with the first diagnostic X-ray 35 (for example at intervals of 100 ms) in a predetermined period. The template image imaging module 52 further controls the second diagnostic X-ray source 25 so that the patient 43 is cyclically irradiated with the second diagnostic X-ray 36 in a predetermined period. The template image imaging module 52 further controls the first sensor array 32 so that a plurality of first frames are generated based on the X-rays passing through the patient 43 when the patient 43 is irradiated with the first diagnostic X-ray 35. The template image imaging module 52 further controls the second sensor array 33 so that a plurality of second frames are generated based on the X-rays passing through the patient 43 when the patient 43 is irradiated with the second diagnostic X-ray 36.

The template generating module 53 calculates a plurality of first templates and a first template position table based on the first frames obtained by the template image imaging module 52. The template generating module 53 further calculates a plurality of second templates and a second template position table based on the second frames obtained by the template image imaging module 52.

The specified image movement range calculating module 54 calculates a first specific-image movement range based on the first template position table calculated by the template generating module 53. The specified image movement range calculating module 54 further calculates a second specific-image movement range based on the second template position table calculated by the template generating module 53.

The template table generating module 55 calculates a first template table based on the plurality of first templates and the first template position table calculated by the template generating module 53 and the first specific-image movement range calculated by the specified image movement range calculating module 54. The template table generating module 55 further calculates a second template table based on the plurality of second templates and the second template position table calculated by the template generating module 53 and the second specific-image movement range calculated by the specified image movement range calculating module 54.

The tracking image imaging module 56 controls the radiation therapy apparatus 3 so that a tracking radiographic image of the patient 43 lying down on the couch 41 is obtained. That is, the tracking image imaging module 56 controls the first diagnostic X-ray source 24 so that the patient 43 is irradiated with the first diagnostic X-ray 35. The tracking image imaging module 56 further controls the second diagnostic X-ray source 25 so that the patient 43 is irradiated with the second diagnostic X-ray 36 at the same time when the patient 43 is irradiated with the first diagnostic X-ray 35. The tracking image imaging module 56 further controls the first sensor array 32 so that a first tracking radiographic image is generated based on X-rays passing through the patient 43 when the patient 43 is irradiated with the first diagnostic X-ray 35. The tracking image imaging module 56 further controls the second sensor array 33 so that a second tracking radiographic image is generated based on X-rays passing through the patient 43 when the patient 43 is irradiated with the second diagnostic X-ray 36.

The matching module 57 refers to the first template table calculated by the template table generating module 55 to calculate a plurality of first degrees of similarity based on the first tracking radiographic image obtained by the tracking image imaging module 56. The first degrees of similarity are associated with a plurality of matching target areas. The plurality of matching target areas are a plurality of areas included in a first predictive range calculated by the predictive range calculating module 59 among all matching target areas that can be defined on the first tracking radiographic image and also included in the first specific-image movement range calculated by the specified image movement range calculating module 54. The matching module 57 refers to the second template table calculated by the template table generating module 55 to calculate a plurality of second degrees of similarity based on the second tracking radiographic image obtained by the tracking image imaging module 56. The plurality of second degrees of similarity are associated with a plurality of matching target areas. The plurality of matching target areas are a plurality of areas included in a second predictive range calculated by the predictive range calculating module 59 among all matching target areas that can be defined on the second tracking radiographic image and also included in the second specific-image movement range calculated by the specified image movement range calculating module 54.

The specified image position calculating module 58 calculates a first specific-image position based on the plurality of first degrees of similarity calculated by the matching module 57. The first specific-image position indicates a position where the area associated with the maximum value of the first degrees of similarity among the matching target areas subjected to matching by the matching module 57 is positioned on the first tracking radiographic image obtained by the tracking image imaging module 56. The specified image position calculating module 58 calculates a second specific-image position based on the plurality of second degrees of similarity calculated by the matching module 57. The second specific-image position indicates a position where the region associated with the maximum value of the second degrees of similarity among the matching target areas subjected to matching by the matching module 57 is positioned on the second tracking radiographic image obtained by the tracking image imaging module 56.

The predictive range calculating module 59 calculates a first predictive range based on the first specific-image position previously calculated by the specified image position calculating module 58. The first predictive range indicates a range obtained through enlargement by a predetermined margin, centering on the previously-calculated first specific-image position. The margin is calculated based on the maximum value of the speed at which the affected area of the patient 43 moves. The predictive range calculating module 59 calculates a second predictive range based on the second specific-image position previously calculated by the specified image position calculating module 58. The second predictive range indicates a range obtained through enlargement by a predetermined margin, centering on the previously-calculated second specific-image position.

The radiation therapy module 60 controls the radiation therapy apparatus 3 so that radiation therapy indicated by the treatment plan obtained by the treatment plan obtaining module 51 is performed. That is, the radiation therapy module 60 calculates a three-dimensional position of the affected area of the patient 43 based on the first specific-image position and the second specific-image position calculated by the specified image position calculating module 58. The radiation therapy module 60 controls the swing device 15 so that the therapeutic radiation ray irradiation device 16 is oriented to the three-dimensional position. The radiation therapy module 60 further calculates the shape of the affected area of the patient 43 based on the first tracking radiographic image and the second tracking radiographic image obtained by the tracking image imaging module 56. The radiation therapy module 60 further controls the multi-leaf collimator 20 so that the shape of the affected area coincides with the irradiation field of the therapeutic radiation ray 23. The radiation therapy module 60 further controls the therapeutic radiation ray irradiation device 16 so that the affected area is irradiated with the therapeutic radiation ray 23. The radiation therapy module 60 further repeatedly performs operations from the imaging of radiographic images to the irradiation of the therapeutic radiation ray 23, until the affected area of the patient 43 is irradiated with the dose of the therapeutic radiation ray 23 indicated by the treatment plan.

Figure 4:
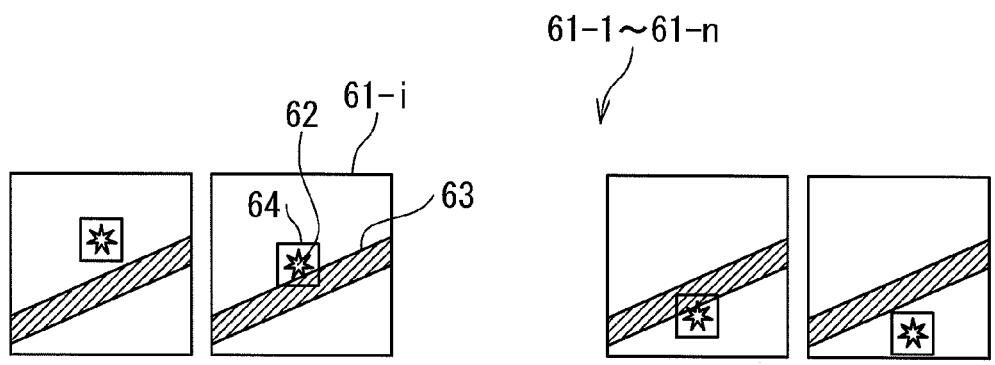
FIG. 4 is a plan view of a plurality of first frames.

FIG. 4 depicts a plurality of first frames obtained by the template image imaging module 52. A plurality of first frames 61-1 to 61-n are obtained so that a moving picture is configured when the first frames 61-1 to 61-n are sequentially displayed one by one. The moving picture displays the patient 43 breathing in a plurality of cycles. Each first frame 61-i of the plurality of first frames 61-1 to 61-n displays a plurality of organs. The plurality of organs include the affected area and a bone of the patient 43. That is, the first frame 61-i displays an affected-area image 62 and a bone image 63. The affected-area image 62 shows the affected area. The bone image 63 shows the bone.

It should be noted that the plurality of first frames 61-1 to 61-n are not necessarily obtained cyclically to be configured as a moving picture, and may be replaced with a plurality of first template generation radiographic images obtained at different timings. The first template generation radiographic images may be obtained at timings at which the phases of respiration of the patient 43 are different, or at timings at which the relative positions between the affected area and the bone of the patient 43 are different, or at timings at which the shapes of the affected area of the patient 43 are different.

Here, the template generating module 53 calculates a plurality of first provisional templates from the plurality of first frames 61-1 to 61-n based on information inputted via the input device. That is, the template generating module 53 selects some of the first frames from the plurality of first frames 61-1 to 61-n based on the information inputted via the input device. The template generating module 53 further specifies a first provisional template candidate area for each of the selected first frames based on the information inputted via the input device. When the first frame 61-i is selected from the plurality of first frames 61-1 to 61-n, the template generating module 53 specifies a first provisional template candidate area 64 in the first frame 61-i based on the information inputted via the input device. The first provisional template candidate area 64 is specified so that only one area is specified in each first frame 61-i to be formed in a predetermined shape and that the entire area where the affected-area image 62 is displayed in the first frame 61-i is included in the first provisional template candidate area 64. The shape is a rectangle, the longitudinal side of the rectangle is parallel to the longitudinal side of the first frame 61-i, and the horizontal side of the rectangle is parallel to the horizontal side of the first frame 61-i. The template generating module 53 calculates a first provisional template based on the first frame 61-i and the first provisional template candidate area 64. The first provisional template represents an image to be displayed in the first provisional template candidate area 64 of the first frame 61-i. The first provisional templates are calculated so as to be congruent with the shape of the first provisional template candidate area 64. The template generating module 53 records the plurality of first provisional templates on the storage device.

In the same way as the calculation of the first provisional templates, the template generating module 53 calculates a plurality of second provisional templates from the plurality of second frames obtained by the template image imaging module 52.

The template generating module 53 calculates a plurality of first templates based on the plurality of first frames 61-1 to 61-n and the corresponding first provisional templates calculated. The first templates include some of the first provisional templates. The first templates correspond to some of first frames 61-1 to 61-n. One first template corresponding to a certain first frame 61-i out of the plurality of first templates is calculated based on the first frame 61-i and the plurality of first provisional templates. When calculating the one first template, the template generating module 53 calculates a plurality of degrees of similarity corresponding to all template candidate areas that can be defined in the first frame 61-i. The one first template represents an image to be displayed in one template candidate area corresponding to the maximum value of the plurality of degrees of similarity among all the template candidate areas. The degree of similarity corresponding to a certain template candidate area among the plurality of degrees of similarity indicates the maximum value of the plurality of degrees of similarity corresponding to the plurality of first provisional templates. The degree of similarity corresponding to the certain first provisional template among the plurality of degrees of similarity indicates a degree with which the first provisional template and the image to be displayed in the template candidate area of the first frame 61-i are similar to each other. As the value of the degree is larger, the image and the first provisional template are more similar to each other.

Figure 5:
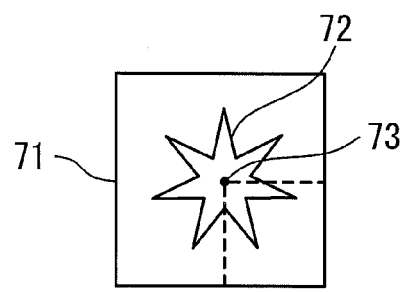
FIG. 5 is a diagram depicting a first template.

FIG. 5 shows one first template out of the plurality of first templates calculated by the template generating module 53. The one first template 71 is formed as a rectangle. The shapes of the plurality of first templates are each congruent with the shape of the first template 71. The first template 71 displays an affected-area image 72. The affected-area image 72 shows the entire affected area of the patient 43. When calculating the first template 71, the template generating module 53 calculates a template center 73. The template center 73 is the center of the first template 71, and is the intersection point of the diagonal lines of the rectangle of the first template 71.

Figure 6:
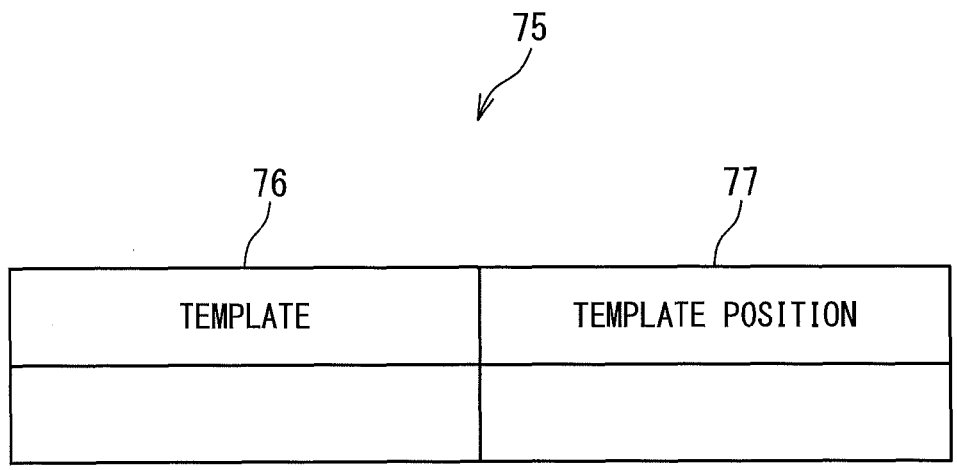
FIG. 6 is a diagram depicting a first template position table.

The template generating module 53 further calculates a first template position table based on the plurality of first templates. FIG. 6 shows a first template position table calculated by the template generating module 53. A first template position table 75 correlates a set of templates 76 with a set of template positions 77. That is, an arbitrary element in the set of templates 76 corresponds to one element in the set of template positions 77. Each element in the set of templates 76 indicates one first template among the plurality of the first templates calculated by the template generating module 53. When the first template is calculated from a certain first frame, an element corresponding to a certain first template in the set of the template positions 77 indicates the center position of the area in the first frame where the first template is displayed.

In the same way as the calculation of the first provisional templates, the template generating module 53 further calculates a plurality of second provisional templates based on the plurality of second frames obtained by the template image imaging module 52 and information inputted via the input device. The template generating module 53 further calculates a plurality of second templates based on the plurality of second provisional templates and the plurality of second frames obtained by the template image imaging module 52, in the same way as the first templates. The template generating module 53 further calculates a second template position table based on the plurality of second templates and the plurality of second frames obtained by the template image imaging module 52, in the same as the first template position table 75.

Figure 7:
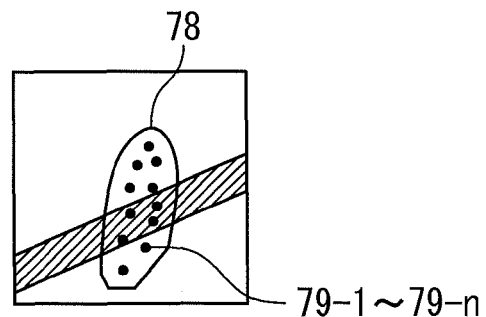
FIG. 7 is a diagram depicting a first specific-image movement range.

FIG. 7 depicts a first specific-image movement range calculated by the specified image movement range calculating module 54. The first specific-image movement range 78 is calculated based on a plurality of positions 79-1 to 79-$n$ indicated by the set of template positions 77 of the first template position table 75. The first specific-image movement range 78 is calculated so as to include all of the plurality of positions 79-1 to 79-$n$ and to include the entire area determined by enlargement from the plurality of positions 79-1 to 79-$n$ by a predetermined margin.

In the same way as the first specific-image movement range 78, the specified image movement range calculating module 54 further calculates a second specific-image movement range based on the second template position table calculated by the template generating module 53.

Figure 8:
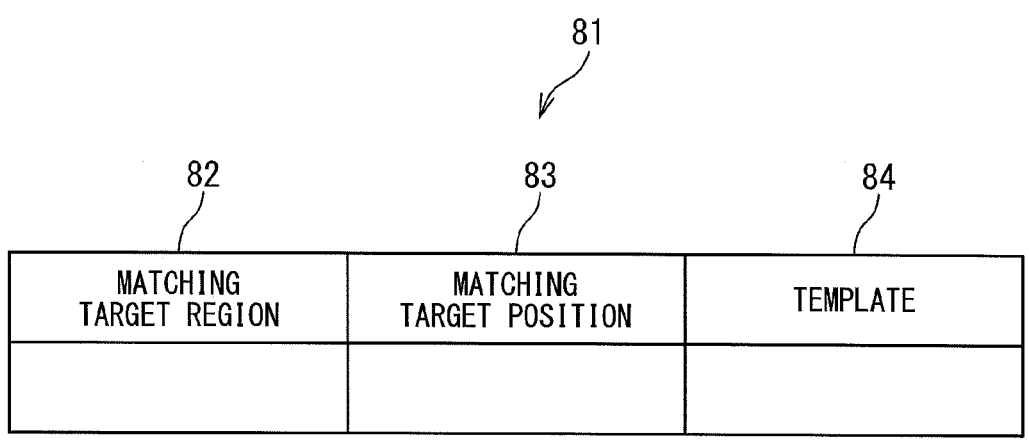
FIG. 8 is a diagram depicting a first template table.

FIG. 8 depicts a first template table calculated by the template table generating module 55. A first template table 81 correlates a set of matching target areas 82 with a set of matching target positions 83, and correlates the set of matching target areas 82 with a set of templates 84. That is, an arbitrary element in the set of matching target areas 82 corresponds to one element in the set of matching target positions 83, and corresponds to one element in the set of templates 84. The set of matching target areas 82 indicate a plurality of matching target areas included in the first specific-image movement range calculated by the specified image movement range calculating module 54 among all the matching target areas that can be defined on the first tracking radiographic image obtained by the tracking image imaging module 56. An element corresponding to a certain matching target area 99 (see FIG. 14) in the set of matching target positions 83 indicates a position where the center of the matching target area of the first tracking radiographic image is placed. The elements of the set of templates 84 indicate a set configured of some of the plurality of first templates calculated by the template generating module 53. The number of first templates belonging to the set is one or more, and not more than an upper-limit count. The upper-limit count is designed so that matching of the first tracking radiographic image obtained by the tracking image imaging module 56 ends within a predetermined time period and, for example, is designed to be four. A first template belonging to the set corresponding to a certain matching target area out of the set of templates 84 is configured of the first template corresponding to the position closest to the center position of the matching target area in the set of templates 76 in the first template position table 75.

Here, the matching module 57 calculates a plurality of first matching target areas included in the first predictive range calculated by the predictive range calculating module 59, when the first tracking radiographic image is obtained by the tracking image imaging module 56. The matching module 57 refers to the first template table 81 to calculate a plurality of first degrees of similarity corresponding to the plurality of first matching target areas. One first degree of similarity corresponding to a certain first matching target area out of the plurality of first degrees of similarity indicates the maximum value of the plurality of degrees of similarity corresponding to the plurality of first templates calculated by the template generating module 53. One degree of similarity corresponding to a certain first template out of the plurality of degrees of similarity indicates a degree with which the first template and an image to be displayed in the first matching target area of the first tracking radiographic image are similar to each other. As the value of the degree is larger, the image and the first template are more similar to each other.

Here, the specified image position calculating module 58 calculates a first specific-image position based on the plurality of first degrees of similarity calculated by the matching module 57. The first specific-image position indicates the center position of one area corresponding to the maximum value of the plurality of first degrees of similarity out of the plurality of first matching target areas, that is, indicates a position corresponding to the maximum value of the plurality of first degrees of similarity in the set of matching target positions 83 of the first template table 81.

In the same way as the first template table 81, the template table generating module 55 calculates a second template table based on the plurality of second templates calculated by the template generating module 53, the second template position table, and the second specific-image movement range calculated by the specified image movement range calculating module 54.

In the same way as the plurality of first degrees of similarity, the matching module 57 further calculates a plurality of second degrees of similarity based on the second tracking radiographic image and the plurality of second templates calculated by the template generating module 53, when the second tracking radiographic image is obtained by the tracking image imaging module 56.

In the same way as the first specific-image position, the specified image position calculating module 58 further calculates a second specific-image position based on the plurality of second degrees of similarity calculated by the matching module 57.

An embodiment of a radiation therapy apparatus control method according to the present invention is implemented by the radiation therapy apparatus controller 2, including a template-table generating operation and a radiation therapy performing operation.

Figure 9:
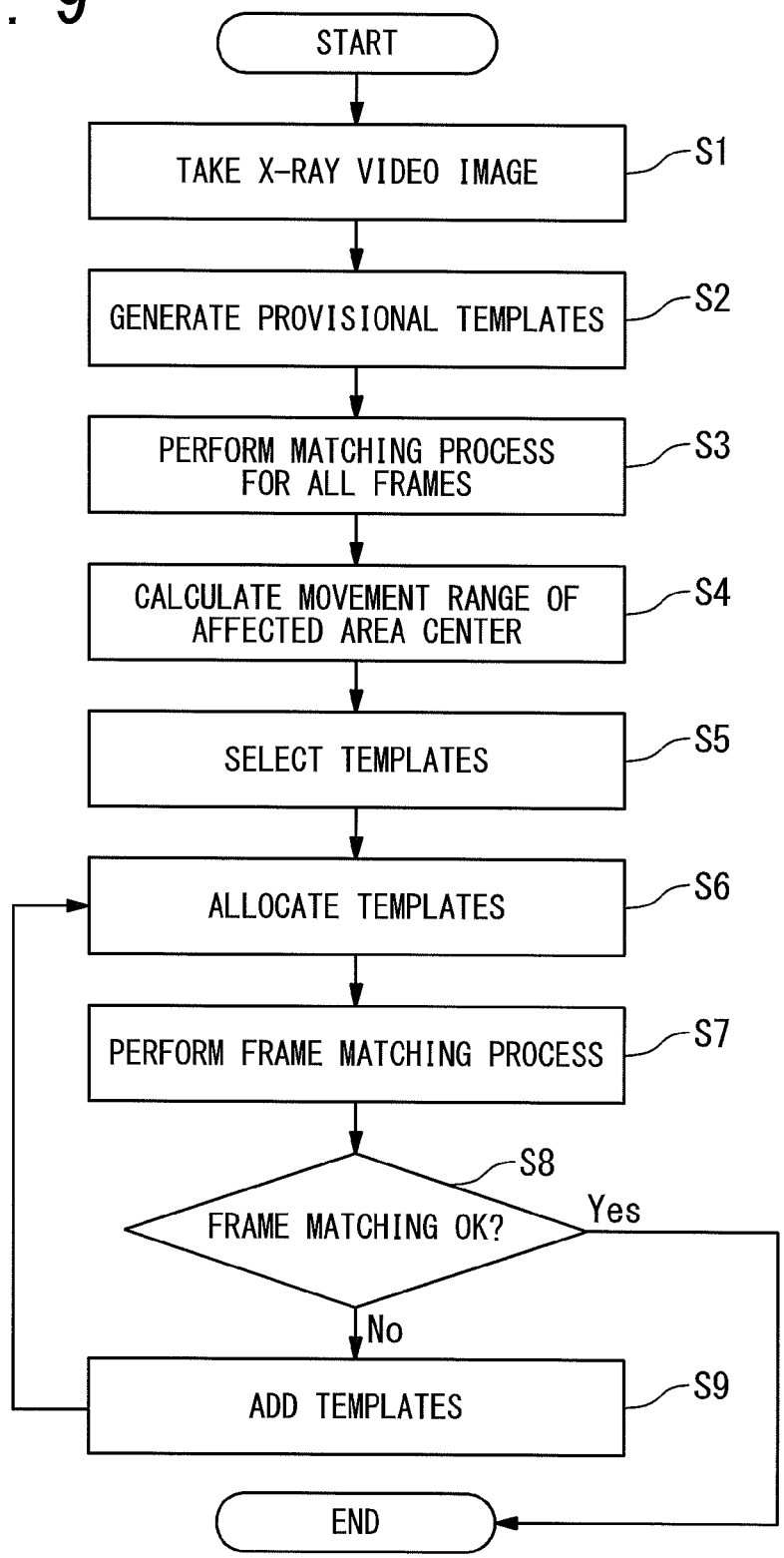
FIG. 9 is a flowchart showing a template-table generation operation.

FIG. 9 depicts a template-table generating operation. First, a user inputs treatment plans previously generated to the radiation therapy apparatus controller 2 via the input device. The treatment plans represent three-dimensional data, showing combinations of irradiation angles and doses. The three-dimensional data correlate a plurality of transmittances associated with a plurality of voxels. The plurality of voxels correspond to a plurality of rectangular parallelepipeds that tightly fill the space where the patient 43 is placed. The transmittance corresponding to each voxel represents an X-ray transmittance of the cube at the position corresponding to the voxel. The three-dimensional data indicate stereoscopic shapes of a plurality of organs of the patient 43 lying down on the bed, and a plurality of positions where the plurality of organs are positioned. The three-dimensional data further indicate a stereoscopic shape of the affected area of the patient 43 lying down on the bed and the position of the affected area. The irradiation angles each indicate a direction in which the affected area of the patient 43 is irradiated with the therapeutic radiation ray 23, indicating a couch position, an O-ring rotation angle, and a gantry rotation angle. The couch positions each indicate the position and orientation of the couch 41 with respect to the base. The O-ring rotation angle indicates the position of the O ring 12 with respect to the base. The gantry rotation angle indicates the position of the running gantry 14 with respect to the O ring 12. The doses each indicate a dose of the therapeutic radiation ray 23 with which the patient 43 is irradiated at each irradiation angle.

The user fixes the patient 43 to the couch 41 of the radiation therapy apparatus 3. The radiation therapy apparatus controller 2 controls the radiation therapy apparatus 3 so that a moving picture displaying the patient 43 lying down on the couch 41 is obtained. That is, the radiation therapy apparatus controller 2 controls the couch drive devise 42 so that the couch 41 is placed at the couch position with respect to the base. The radiation therapy apparatus controller 2 further controls the swivel drive device 11 so that the O ring 12 is placed at the O-ring rotation angle with respect to the base. The radiation therapy apparatus controller 2 further controls the running drive device of the radiation therapy apparatus 3 so that the running gantry 14 is placed at the gantry rotation angle. The radiation therapy apparatus controller 2 further controls the first diagnostic X-ray source 24 so that the patient 43 is cyclically irradiated with the first diagnostic X-ray 35 (for example at intervals of 100 ms) in a predetermined period. The radiation therapy apparatus controller 2 further controls the second diagnostic X-ray source 25 so that the patient 43 is cyclically irradiated with the second diagnostic X-ray 36 in a predetermined period. The radiation therapy apparatus controller 2 further controls the first sensor array 32 so that the plurality of first frames 61-1 to 61-n are generated based on X-rays passing through the patient 43 when the patient 43 is irradiated with the first diagnostic X-ray 35. The radiation therapy apparatus controller 2 further controls the second sensor array 33 so that a plurality of second frames are generated based on X-rays passing through the patient 43 when the patient 43 is irradiated with the second diagnostic X-ray 36 (step S1).

The user selects appropriate ones of first provisional template frames from among the plurality of first frames 61-1 to 61-n. The first provisional template frames are a plurality of first frames obtained at timings at which phases of respiration of the patient 43 are different, or a plurality of first frames obtained at timings at which the relative positions between the affected area and the bone of the patient 43 are different, or a plurality of first frames at timings at which the shapes of the affected area of the patient 43 are different. The user inputs the plurality of the first provisional template frames to the radiation therapy apparatus controller 2 via the input device. The user further specifies a first provisional template candidate area for each of the plurality of first provisional template frames. The first provisional template candidate area 64 specified in one first provisional template frame 61-i out of the plurality of first provisional template frames includes an area where the entire affected-area image 62 is displayed. The user inputs the plurality of first provisional template candidate areas to the radiation therapy apparatus controller 2 via the input device.

The radiation therapy apparatus controller 2 calculates a plurality of first provisional templates based on the selected first provisional template frames and the specified first provisional template candidate areas (step S2). A first provisional template calculated based on a certain first provisional template frame and a certain first provisional template candidate area among the plurality of first provisional templates represents an image to be displayed in the first provisional template candidate area of the first provisional template frame.

The user selects a plurality of second provisional template frames in the same way as the first provisional template frames, and selects a plurality of second provisional template candidate areas in the same way as the first provisional template candidate areas. In the same way as the plurality of first provisional templates, the radiation therapy apparatus controller 2 calculates a plurality of second provisional templates based on the plurality of second provisional template frames and the plurality of the second provisional template candidate areas.

The radiation therapy apparatus controller 2 calculates a plurality of first templates corresponding to the plurality of first frames 61-1 to 61-n based on the calculated plurality of first provisional templates (step S3). One first template corresponding to a certain first frame 61-i out of the plurality of first templates is calculated based on the first frame 61-i and the plurality of first provisional templates. When calculating the one first template, the radiation therapy apparatus controller 2 calculates a plurality of degrees of similarity corresponding to all the template candidate areas that can be defined in the first frame 61-i. The one first template represents an image displayed in one template candidate area corresponding to the maximum value of the plurality of degrees of similarity among all the template candidate areas. The degree of similarity corresponding to a certain template candidate area out of the plurality of degrees of similarity indicates the maximum value of the plurality of degrees of similarity corresponding to the plurality of first provisional templates. The degree of similarity corresponding to a certain first provisional template among the plurality of degrees of similarity indicates a degree with which the first provisional template and the image displayed in the template candidate area of the first frame 61-i are similar to each other. The radiation therapy apparatus controller 2 further calculate the first template position table 75 based on the first provisional template candidate areas and the template candidate areas.

The radiation therapy apparatus controller 2 calculates a plurality of second templates corresponding to the plurality of second frames obtained at step S1 based on the plurality of second provisional templates in the same way as the plurality of first templates, and calculates a second template position table in the same way as the first template position table 75.

The radiation therapy apparatus controller 2 calculates a first specific-image movement range 78 based on the first template position table 75 (step S4). The radiation therapy apparatus controller 2 further calculates a second specific-image movement range based on the second template position table.

The radiation therapy apparatus controller 2 selects appropriate one of first templates from the plurality of first templates calculated at step S3 (step S5). The selected ones of first templates are selected so that the degrees of similarity therebetween are smaller than a predetermined threshold. The radiation therapy apparatus controller 2 further selects appropriate ones of second templates from the plurality of second templates calculated at step S3.

The radiation therapy apparatus controller 2 calculates a plurality of first matching target areas based on the first specific-image movement range 78. The plurality of first matching target areas represent a plurality of areas included in the first specific-image movement range 78 out of all the first matching target areas that can be defined in the first radiographic image obtained by the first sensor array 32. The radiation therapy apparatus controller 2 further correlates the plurality of first templates to the plurality of first matching target areas to generate the first template table 81 (step S6). That is, the radiation therapy apparatus controller 2 generates the first template table 81 so that the first template at the position closest to the center position of a certain first matching target area in the set of templates 76 in the first template position table 75 corresponds to the first matching target area.

The radiation therapy apparatus controller 2 calculates a plurality of first degrees of similarity associated with the plurality of first frames 61-1 to 61-*n* based on the plurality of first templates correlated at step S6 (step S7). The first degree of similarity corresponding to a certain first frame out of the plurality of first degrees of similarity indicates the maximum value of the plurality of degrees of similarity associated with all the matching target areas included in the first specific-image movement range 78. The degree of similarity corresponding to a certain matching target area out of the plurality of degrees of similarity indicates the maximum value of the plurality of degrees of similarity corresponding to the plurality of first templates assigned at step S6. The degree of similarity corresponding to a certain first template among the plurality of degrees of similarity indicates a degree with which an image displayed in the matching target area of the first frame and the first template are similar to each other. As the value of the degree is larger, the image and the first template are more similar to each other.

When the plurality of first degrees of similarity include a value smaller than a predetermined threshold (NO at step S8), the radiation therapy apparatus controller 2 adds to the plurality of first templates selected at step S5, the first template calculated from the first frame corresponding to the small first degree of similarity among the plurality of first frames 61-1 to 61-*n* (step S9). When the center position of the added first template is closer to the center position of the first matching target area compared with the center position of the first template correlated to a certain first matching target area at step S6, the radiation therapy apparatus controller 2 further additionally correlates the added first template to the first matching target area. When the number of first templates assigned to the first matching target area exceeds an upper limit number, the radiation therapy apparatus controller 2 further deletes the first template correlated to the first matching target area and having the center position farthest from the plurality of first templates. Next, the radiation therapy apparatus controller 2 performs step 7 to step 8 again.

In the same way as the first template table 81, the radiation therapy apparatus controller 2 calculates a second template table based on the plurality of second templates, the plurality of second template position tables, the second specific-image movement range, and the plurality of second frames obtained at step S1.

Figure 10:
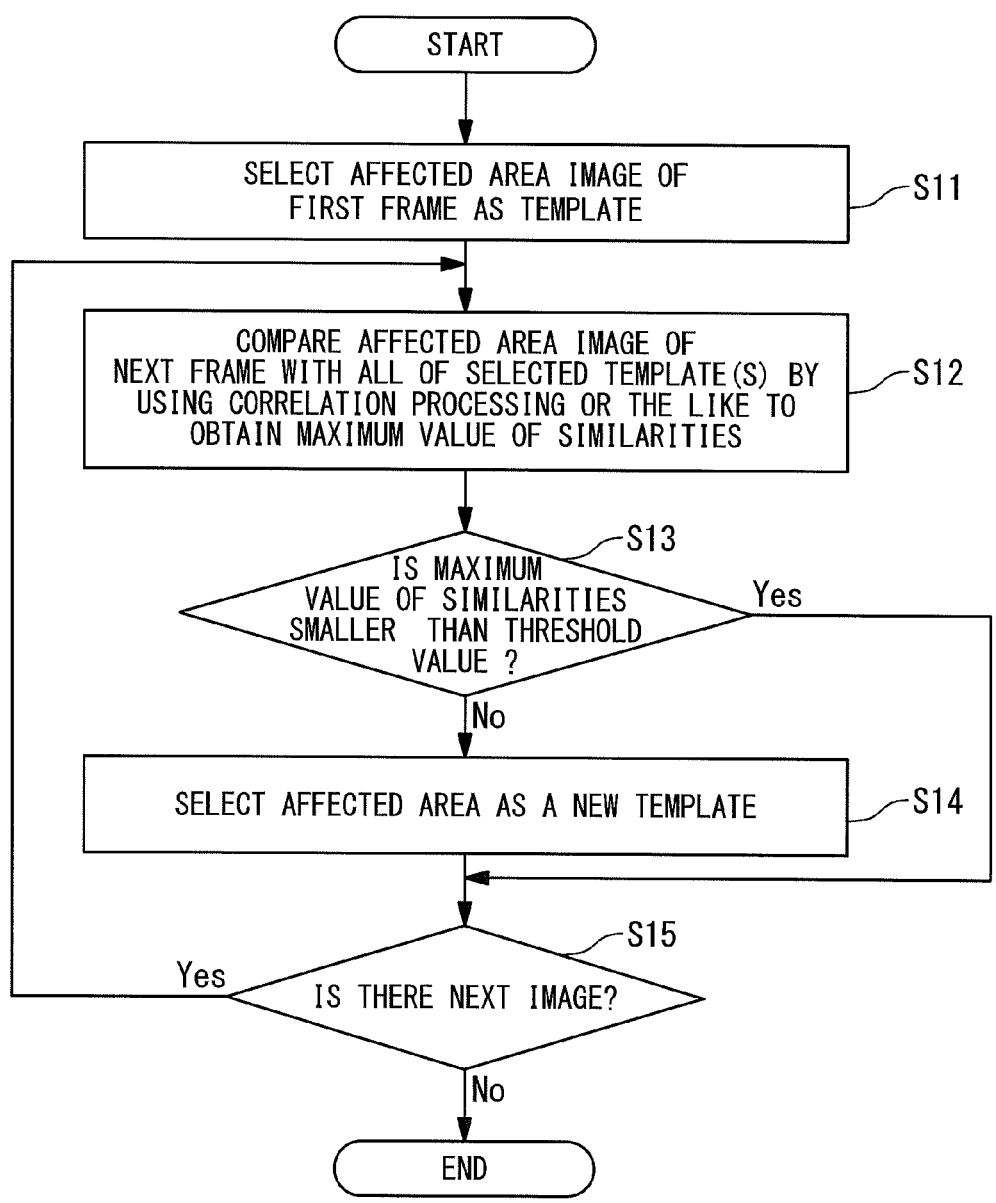
FIG. 10 is a flowchart depicting a template selecting operation.

FIG. 10 depicts the process at step S5. The radiation therapy apparatus controller 2 first selects an initial first frame 61-1 from among the plurality of first frames 61-1 to 61-*n*, and adds a first template calculated from the selected first frame 61-1 to a first template set (step S11).

The radiation therapy apparatus controller 2 calculates a plurality of first degrees of similarity based on the first template set and a next first frame next to the selected first frame among the plurality of first frames 61-1 to 61-*n*. The plurality of first degrees of similarity correspond to all the first matching target areas that can be defined in the next first frame. The degree of similarity corresponding to a certain first matching target area out of the plurality of degrees of similarity indicates the maximum value of the plurality of degrees of similarity corresponding to the first template set. The degree of similarity corresponding to a certain first template out of the plurality of degrees of similarity indicates a degree with which the first template and an image to be displayed in the first matching target area in the next first frame.

When the maximum value of the plurality of first degrees of similarity is larger than a predetermined threshold (NO at step S13), the radiation therapy apparatus controller 2 adds a first template calculated from the next first frame to the first template set (step S14).

When the maximum value of the plurality of first degrees of similarity is smaller than the predetermined threshold (YES at step S13) or after step S14 is performed, the radiation therapy apparatus controller 2 determines whether a first frame next to the next first frame is present out of the plurality of first frames 61-1 to 61-*n* (step S15). When the next first frame is present (YES at step S15), the radiation therapy apparatus controller 2 selects that first frame, and performs the processes from step S12 to step S14 again.

The radiation therapy operation is performed after the template-table generating operation is completed. That is, after the couch 41, the O ring 12, and the running gantry 14 are placed at each predetermined positions, the radiation therapy apparatus controller 2 controls the first diagnostic X-ray source 24 and the first sensor array 32 so that a first tracking radiographic image of the patient 43 is obtained, and controls the second diagnostic X-ray source 25 and the second sensor array 33 so that a second tracking radiographic image of the patient 43 is obtained.

The radiation therapy apparatus controller 2 refers to the first template table 81 to calculate a plurality of first degrees of similarity corresponding to the plurality of first matching target areas indicated by the matching target area set 82 based on the first tracking radiographic image. The first degree of similarity corresponding to a certain first matching target area among the plurality of first degrees of similarity indicates the maximum value of the plurality of degrees of similarity corresponding to the first template belonging to the set corresponding to the matching target area in the template set 84. The degree of similarity corresponding to a certain first template among the plurality of degrees of similarity indicates a degree with which an image to be displayed in the matching target area of the first tracking radiographic image is similar to the first template. As the value of the degree is larger, the image and the first template are more similar to each other.

The radiation therapy apparatus controller 2 calculates the first matching target area corresponding to the maximum value of the plurality of first degrees of similarity out of the plurality of first matching target areas, and calculates a first specific-image position based on the calculated first matching target area. The first specific-image position indicates a matching target position corresponding to the first matching target area in the matching target position set 83.

After calculating the first specific-image position once, the radiation therapy apparatus controller 2 calculates a first predictive range based on the first specific-image position. The first predictive range represents a range enlarged by a predetermined margin, centering on the calculated first specific-image position. Here, the radiation therapy apparatus controller 2 refers to the first template table 81 to calculate the plurality of first degrees of similarity corresponding to the plurality of first matching target areas included in the first predictive range out of the plurality of first matching target areas indicated by the matching target area set 82. The first degree of similarity corresponding to a certain first matching target area out of the plurality of first degrees of similarity indicates the maximum value of the plurality of degrees of similarity corresponding to the first template belonging to the set corresponding to the matching target area in the template set 84. The degree of similarity corresponding to a certain first template among the plurality of degrees of similarity indicates a degree with which an image to be displayed in the matching target area of the first tracking radiographic image is similar to the first template. As the value of the degree is larger, the image and the first template are more similar to each other.

The radiation therapy apparatus controller 2 calculates a first matching target area corresponding to the maximum value of the first degrees of similarity out of the plurality of first matching target areas, and calculates a first specific-image position based on the calculated first matching target area. The first specific-image position indicates a matching target position corresponding to the first matching target area out of the set of matching target positions 83.

Furthermore, the radiation therapy apparatus controller 2 refers to the second template table to calculate a second specific-image position based on the second tracking radiographic image, in the same way as the first specific-image position.

The radiation therapy apparatus controller 2 calculates a first straight line based on the first specific-image position. The first straight line is a straight line connecting the vertex of the cone beam of the first diagnostic X-ray 35 and a position corresponding to the first specific-image position in the light-receiving portion of the first sensor array 32. The radiation therapy apparatus controller 2 calculates a second straight line based on the second specific-image position. The second straight line is a straight line connecting the vertex of the cone beam of the second diagnostic X-ray 36 and a position corresponding to the second specific-image position in the light-receiving portion of the second sensor array 33. The radiation therapy apparatus controller 2 calculates a three-dimensional position of the affected area of the patient 43 based on the first straight line and the second straight line. The three-dimensional position indicates the position of the midpoint of a line segment connecting a first point on the first straight line closest to the second straight line and a second point on the second straight line closest to the first straight line. The radiation therapy apparatus controller 2 calculates a drive amount based on the three-dimensional position. The drive amount includes a tilt-axis rotation amount and a pan-axis rotation amount. The drive amount is calculated so that the therapeutic radiation ray irradiation device 16 is oriented toward the three-dimensional position when the therapeutic radiation ray irradiation device 16 rotates about the tilt axis 21 by the tilt-axis rotation amount and the therapeutic radiation ray irradiation device 16 rotates about the pan axis 22 by the pan-axis rotation amount. The radiation therapy apparatus controller 2 controls the swing device 15 so that the therapeutic radiation ray irradiation device 16 rotates about the tilt axis 21 by the tilt-axis rotation amount and the therapeutic radiation ray irradiation device 16 rotates about the pan axis 22 by the pan-axis rotation amount.

The radiation therapy apparatus controller 2 calculates the shape of the affected area of the patient 43 based on the first tracking radiographic image and the second tracking radiographic image. The radiation therapy apparatus controller 2 controls the multi-leaf collimator 20 so that the shape of the affected area coincides with the irradiation field of the therapeutic radiation ray 23. After controlling the swing device 15 and the multi-leaf collimator 20, the radiation therapy apparatus controller 2 controls the therapeutic radiation ray irradiation device 16 so that the affected area is irradiated with the therapeutic radiation ray 23. The radiation therapy apparatus controller 2 further repeatedly and cyclically performs the operations of imaging of the first tracking radiographic image and the second tracking radiographic image to irradiation of the therapeutic radiation ray 23 until the affected area of the patient 43 is irradiated with the dose of the therapeutic radiation ray 23 indicated by the treatment plan. One example of the cycle is 0.2 seconds.

According to the above-described radiation therapy apparatus control method, the radiation therapy apparatus controller 2 can perform matching of the plurality of different templates with the plurality of different matching target areas in the tracking radiographic image, and can perform matching of a plurality of appropriate templates with the plurality of matching target areas in the tracking radiographic image. Therefore, the radiation therapy apparatus controller 2 can increase the number of templates for use in matching, and can reduce the number of templates for matching with the plurality of matching target areas. As a result, the radiation therapy apparatus controller 2 can more reliably and more accurately calculate the specific-image position. As a result, the radiation therapy apparatus controller 2 can more accurately calculate the drive amount for driving the therapeutic radiation ray irradiation device 16 at higher speed, and can more reliably and more accurately drive the therapeutic radiation ray irradiation device 16.

Figure 11:
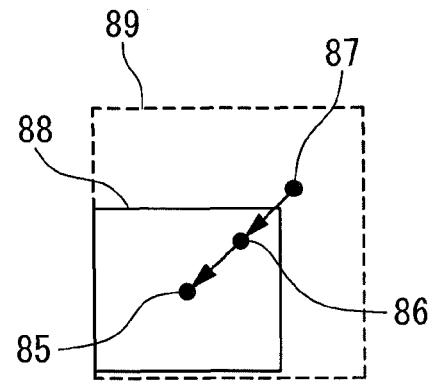
FIG. 11 is a diagram depicting another first predictive range.

In another embodiment of the radiation therapy apparatus controller according to the present invention, the predictive range calculating module 59 in the above-described embodiment is replaced with another predictive-range calculating module. FIG. 11 depicts a first predictive range calculated by a first predictive range calculating module. The first predictive range calculating module calculates a first predictive position 85 based on a first specific-image position 86 immediately previously calculated by the specified image position calculating module 58 and a first specific-image position 87 calculated by the specified image position calculating module 58 immediately previously to the first specific-image position 86. The first predictive position 85 is calculated so that a point internally dividing the first predictive position 85 and the first specific-image position 87 at a ratio of 1:1 coincides with the first specific-image position 86. The first predictive range calculating module calculates a first predictive range 88 based on the first predictive position 85. The first predictive range 88 indicates a range enlarged by a predetermined margin, centering on the first predictive position 85. Here, the margin can be smaller than the margin for use in the predictive range calculating module 59. Therefore, the first predictive range 88 can be formed smaller compared with the first predictive range 89 calculated by the predictive range calculating module 59.

As is the case of the radiation therapy apparatus controller 2 in the above-described embodiment, this radiation therapy apparatus controller can more reliably and more accurately drive the therapeutic radiation ray irradiation device 16. Furthermore, compared with the radiation therapy apparatus controller 2 in the above-described embodiment, this radiation therapy apparatus controller can further reduce the number of the plurality of matching target areas for matching, and can calculate the first specific-image position at higher speed. As a result, compared with the radiation therapy apparatus controller 2 in the above-described embodiment, this radiation therapy apparatus controller can calculate the position of the affected area of the patient 43 at higher speed, and can more reliably and more accurately drive the therapeutic radiation ray irradiation device 16.

Figure 12:
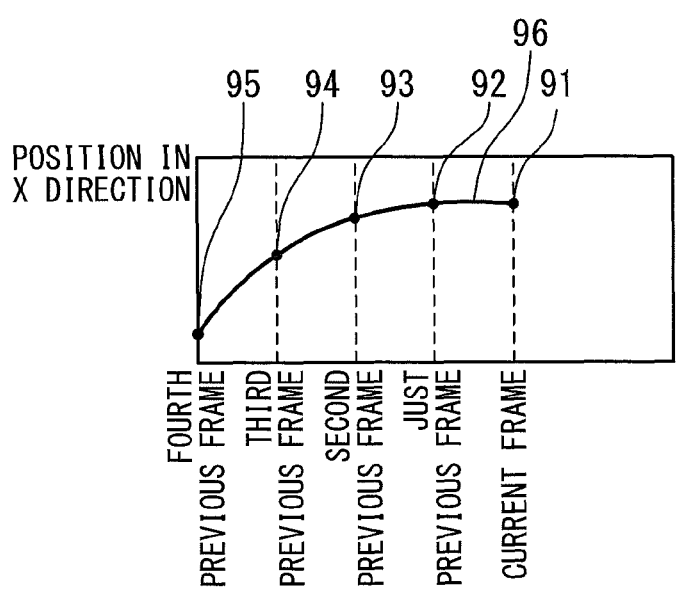
FIG. 12 is a diagram depicting x coordinates of still another first predictive range.

In still another embodiment of the radiation therapy apparatus controller according to the present invention, the predictive range calculating module 59 in the above-described embodiment is replaced with still another predictive-range calculating module. A first predictive-range calculating module calculates a first predictive range based on the plurality of first specific-image positions immediately previously calculated by the specified image position calculating module 58. The immediately-previously calculated first specific-image positions include, as depicted in FIG. 12, a position 92, a position 93, a position 94, and a position 95. The position 92 indicates the x coordinate of the immediately-previously calculated first specific-image position. The position 93 indicates the x coordinate of a first specific-image position calculated immediately previously to the first specific-image position indicating the position 92. The position 94 indicates the x coordinate of a first specific-image position calculated immediately previously to the first specific-image position indicating the position 93. The position 95 indicates the x coordinate of a first specific-image position calculated immediately previously to the first specific-image position indicating the position 94. The first predictive-range calculating module calculates a spline curve 96 passing through the position 92, the position 93, the position 94, and the position 95. The first predictive-range calculating module calculates a predictive x coordinate 91 based on the spline curve 96. The predictive x coordinate 91 is calculated so as to pass through the spline curve 96. In the same way as the predictive x coordinate 91, the first predictive-range calculating module calculates a predictive y coordinate. The first predictive-range calculating module calculates a first predictive range based on the predictive x coordinate and the predictive y coordinate. The first predictive range indicates a range enlarged by a predetermined margin, centering on the position indicated by the predictive x coordinate and the predictive y coordinate. Here, the margin can be smaller than the margin for use in calculating the first predictive range 88. Therefore, the first predictive range can be formed smaller compared with the first predictive range 88.

As is the case of the radiation therapy apparatus controller 2 in the above-described embodiment, this radiation therapy apparatus controller can drive the therapeutic radiation ray irradiation device 16 more reliably and accurately. Furthermore, compared with the radiation therapy apparatus controller 2 in the above-described embodiment, this radiation therapy apparatus controller can further reduce the number of the plurality of matching target areas for matching, and can calculate the first specific-image position at higher speed. As a result, compared with the radiation therapy apparatus controller 2 in the above-described embodiment, this radiation therapy apparatus controller can calculate the position of the affected area of the patient 43 at higher speed, and can drive the therapeutic radiation ray irradiation device 16 more reliably and accurately.

In still another embodiment of the radiation therapy apparatus controller according to the present invention, the template image imaging module 52 in the above-described embodiment is replaced with another template image imaging module, and the specified image movement range calculating module 54 in the above-described embodiment is replaced with another specific-image movement range calculating module.

Figure 13:
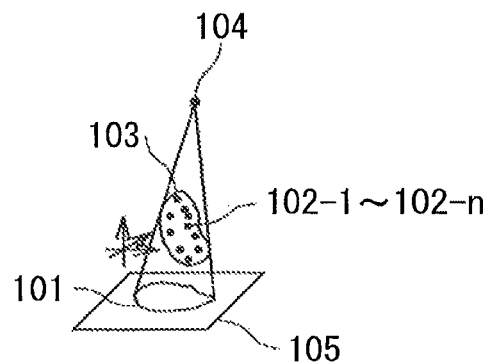
FIG. 13 is a diagram depicting a three-dimensional specific-area movement range.

As depicted in FIG. 13, the template image imaging module controls the first diagnostic X-ray source 24 and the first sensor array 32 so that the plurality of first frames 61-1 to 61-*n* are obtained at a plurality of different times. The template image imaging module further controls the second diagnostic X-ray source 25 and the second sensor array 33 so that the plurality of second frames are obtained at a plurality of different times.

The specific-image movement range calculating module calculates a plurality of affected-area positions 102-1 to 102-*n* based on the first template position table 75 and the second template position table generated by the template generating module 53. That is, when calculating a certain affected-area position corresponding to a certain time out of the affected-area positions 102-1 to 102-*n*, the specific-image movement range calculating module calculates a first straight line based on the first template calculated from the first frame obtained at that time out of the plurality of first frames 61-1 to 61-*n*, and calculates a second straight line based on the second template calculated from the second frame obtained at that time out of the plurality of second frames. The first straight line is a straight line connecting the vertex of the cone beam of the first diagnostic X-ray 35 and a position corresponding to the template position of the first template in the light-receiving portion of the first sensor array 32. The second straight line is a straight line connecting the vertex of the cone beam of the second diagnostic X-ray 36 and a position corresponding to the template position of the second template in the light-receiving portion of the second sensor array 33. One affected-area position indicates the position of the midpoint of a line segment connecting the first point on the first straight line closest to the second straight line and the second point on the second straight line closest to the first straight line.

The specific-image movement range calculating module calculates a three-dimensional specific-region movement range 103 based on the plurality of affected-area positions 102-1 to 102-*n*. The three-dimensional specific-region movement range 103 is calculated so as to include all of the plurality of affected-area positions 102-1 to 102-*n* and include entire areas enlarged by a predetermined margin from the plurality of affected-area positions 102-1 to 102-*n*. The specific-image movement range calculating module calculates a first specific-image movement range based on the three-dimensional specific-region movement range 103. The first specific-image movement range is calculated so as to correspond to an area 101 where the three-dimensional specific-region movement range 103 is projected from the point 104 corresponding to the vertex of the cone beam of the first diagnostic X-ray 35 to a plane 105 corresponding to the light-receiving module of the first sensor array 32. In the same way as the first specific-image movement range, the specific-image movement range calculating module calculates a second specific-image movement range based on the three-dimensional specific-region movement range 103.

As is the case of the radiation therapy apparatus controller 2 in the above-described embodiment, this radiation therapy apparatus controller can drive the therapeutic radiation ray irradiation device 16 more reliably and accurately. Furthermore, compared with the radiation therapy apparatus controller 2 in the above-described embodiment, this radiation therapy apparatus controller can more accurately calculate a reduced first specific-image movement range and second specific-image movement range, can reduce the number of the plurality of matching target areas for matching, and can calculate the first specific-image position at higher speed. As a result, compared with the radiation therapy apparatus controller 2 in the above-described embodiment, this radiation therapy apparatus controller can calculate the position of the affected area of the patient 43 at higher speed, and can drive the therapeutic radiation ray irradiation device 16, more reliably and accurately.

In still another embodiment of the radiation therapy apparatus controller according to the present invention, the template generating module 53 in the above-described embodiment is replaced by another template generating module.

Figure 14:
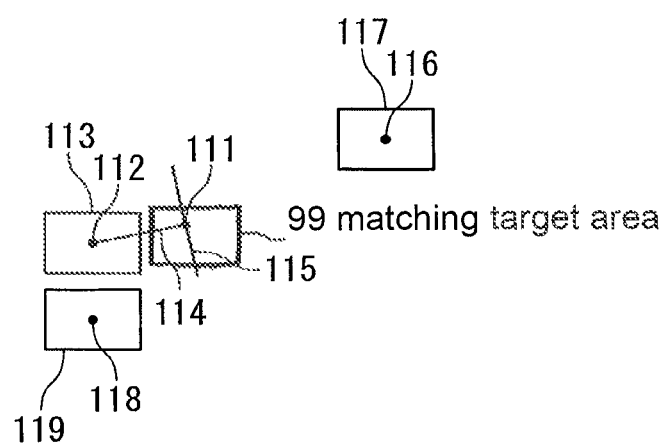
FIG. 14 is a diagram depicting relative positions between a position of a template and a position of a matching target area.

When calculating a set of templates corresponding to the first matching target area out of the set of templates 83 of the first template table 81, as depicted in FIG. 14, the template generating module calculates a template position 112 based on a first matching target position 111 corresponding to the first matching target area. The template position 112 indicates a template position closest to the first matching target position 111 in the set of template positions 77 of the first template position table 75. The template generating module calculates a straight line 115 based on the first matching target position 111 and the template position 112. The straight line 115 is perpendicular to a straight line 114 passing through the first matching target position 111 and the template position 112, and passes through the first matching target position 111. Based on the straight line 115, the template generating module divides the two-dimensional space into two, the two-dimensional space having a template position indicated by the template position set 77 and a matching target position indicated by the matching target position set 82 of the first template table 81 as elements. The template generating module calculates a plurality of template positions included in an area not including the template position 112 from out of these two areas obtained through division into two pieces. The template generating module calculates the template position 116 closest to the first matching target position 111 from the calculated plurality of template positions. The template generating module generates the first template table 81 so that the first template 113 corresponding to the template position 112 in the first template position table 75 corresponds to the first matching target position 111 and that the first template 117 corresponding to the template position 116 in the first template position table 75 corresponds to the first matching target position 111.

That is, the template generating module generates the first template table 81 so that, when the angle formed between the two vectors directed from the first matching target position 111 to the two template positions is equal to or greater than 90 degrees and when these two template positions are close to the first matching target position 111, two first templates corresponding to these two template positions correspond to the first matching target position 111.

When the upper-limit count is three or more, the template generating module further calculates a template position 118 based on the first matching target position 111. The template position 118 indicates a template position next closest to the first matching target position 111 after the template position 112 in the template position set 77. The template generating module generates the first template table 81 so that a first template 119 corresponding to the template position 118 in the first template position table 75 corresponds to the first matching target position 111.

As is the case of the radiation therapy apparatus controller 2 in the above-described embodiment, this radiation therapy apparatus controller can drive the therapeutic radiation ray irradiation device 16 more reliably and accurately. Furthermore, in this radiation therapy apparatus controller, compared with the radiation therapy apparatus controller 2 in the above-described embodiment, the variety of affected-area images shown by the plurality of templates corresponding to one matching target area is increased, thereby making it possible to calculate a specific image position more reliably and accurately. As a result, compared with the radiation therapy apparatus controller 2 in the above-described embodiment, this radiation therapy apparatus controller can drive the therapeutic radiation ray irradiation device 16, more reliably and accurately.

The invention claimed is:

1. A radiation therapy apparatus control method of using a radiation therapy apparatus controller as part of a computer for controlling a therapeutic radiation ray irradiation device that irradiates a target subject with a therapeutic radiation ray, the radiation therapy apparatus control method comprising:
   calculating, via the radiation therapy apparatus controller, a plurality of degrees of similarity corresponding to a plurality of matching target areas based on a radiographic image in which the target subject is imaged;
   calculating, via the radiation therapy apparatus controller, a specific image position where a specific image area is positioned in the radiographic image, the specific image area (i) corresponding to a degree of similarity having a maximum value of the plurality of degrees of similarity and (ii) being an area from the plurality of matching target areas; and
   calculating, via the radiation therapy apparatus controller, a drive amount with which the therapeutic radiation ray irradiation device irradiates the target subject with the therapeutic radiation ray is driven, the drive amount being calculated based on the calculated specific image position,
   wherein, when one of the plurality of degrees similarity corresponding to one of the plurality of matching target areas is calculated by said calculating of the plurality of degrees of similarity, said calculating of the plurality of degrees of similarity:
      refers to a template table in which the matching target areas are associated with a plurality of sets of templates, so as to select, from the plurality of sets of templates, a set of templates corresponding to the one matching target area; and
      detects, from the selected set of templates, a similar template most similar to a matching target image displayed in the one matching target area of the radiographic image, and wherein the one degree of similarity indicates a degree of similarity with which the one matching target image is similar to the similar template,
   wherein the radiation therapy apparatus control method further comprises generating the template table based on all templates generated from a plurality of template generation radiographic images obtained at a plurality of different times by an imager imaging the radiographic image and a plurality of template positions where all of the generated templates are displayed in the plurality of template generation radiographic images,
   wherein each of the plurality of template generation radiographic images is divided into a first area and a second area with a straight line passing through one matching target position where the one matching target area is positioned in the radiographic image,
   wherein the set of templates includes:
      a first template, of all of the generated templates, displayed in the first area;
      and a second template, of all of the generated templates, displayed in the second area, and
   wherein the straight line passing through the one matching target position is perpendicular to a straight line connecting the first template position and the one matching target position.

2. The radiation therapy apparatus control method according claim 1, further comprising calculating a specific-image movement range based on the plurality of template positions, wherein the matching target areas are areas included in the specific-image movement range out of all matching target areas.

3. The radiation therapy apparatus control method according to claim 2, further comprising calculating a three-dimensional specific-region movement range based on a plurality of other template generation radiographic images obtained by another imager different from the imager at the plurality of times and the plurality of template generation radiographic images, wherein the specific-image movement range is calculated based on the three-dimensional specific-region movement range.

4. The radiation therapy apparatus control method according to claim 3, further comprising calculating another specific image position based on another radiographic image obtained by the other imager at a time when the radiographic image is imaged, wherein the drive amount is calculated further based on the other specific image position.

5. The radiation therapy apparatus control method according to claim 1, further comprising calculating a predictive range based on a previous specific image position calculated based on a previous radiographic image obtained at a time previous to a time when the radiographic image is imaged, wherein the matching target areas are areas included in the predictive range out of all matching target areas that can be placed in the radiographic image.

6. A radiation therapy apparatus controller for controlling a therapeutic radiation ray irradiation device that irradiates a target subject with a therapeutic radiation ray, the radiation therapy apparatus controller, as part of a computer, comprising:

a matching module which calculates a plurality of degrees of similarity corresponding to a plurality of matching target areas based on a radiographic image in which the target subject is imaged;

a specific-image position calculating module which calculates a specific image position where a specific image area is positioned in the radiographic image, the specific image area (i) corresponding to a degree of similarity having a maximum value of the plurality of degrees of similarity and (ii) being an area from the plurality of matching target areas; and a radiation therapy module which controls a driving device that drives the therapeutic radiation ray irradiation device that irradiates the target subject with the therapeutic radiation ray based on the calculated specific image position, wherein, when one of the plurality of degrees of similarity corresponding to one of the plurality of matching target areas is calculated by said matching module:

refers to a template table in which the matching target areas are associated with a plurality of sets of templates, so as to select, from the plurality of sets of templates, a set of templates corresponding to the one matching target area; and determines, from the selected set of templates, a similar template most similar to a matching target image displayed in the one matching target area of the radiographic image, wherein the one degree of similarity indicates a degree of similarity with which the one matching target area is similar to the similar template, wherein the radiation therapy apparatus controller further comprises a template table generating module which generates the template table based on all templates generated from a plurality of template generation radiographic images obtained at a plurality of different times by an imager imaging the radiographic image and a plurality of template positions where all of the generated templates are displayed in the plurality of template generation radiographic images, wherein each of the plurality of template generation radiographic images is divided into a first area and a second area with a straight line passing through one matching target position where the one matching target area is positioned in the radiographic image, wherein the set of templates includes:

a first template, of all of the generated templates, displayed in the first area; and a second template, of all of the generated templates, displayed in the second area, and wherein the straight line passing through the one matching target position is perpendicular to a straight line connecting the first template position and the one matching target position.

7. The radiation therapy apparatus controller according to claim 4, wherein said radiation therapy module controls the therapeutic radiation ray irradiation device so that the target subject is irradiated with the therapeutic radiation ray after the therapeutic radiation ray irradiation device is driven.

8. The radiation therapy apparatus controller according to claim 4, further comprising a specific-image movement range calculating module which calculates a specific-image movement range based on a plurality of template positions, wherein the matching target areas are areas included in the specific-image movement range out of all matching target areas.

9. The radiation therapy apparatus controller according to claim 8, wherein the specific-image movement range calculating module:

calculates a three-dimensional specific-region movement range based on a plurality of other template generation radiographic images obtained by another imager different from the imager at the plurality of times and the plurality of template generation radiographic images; and calculates the specific-image movement range based on the three-dimensional specific-region movement range.

10. The radiation therapy apparatus controller according to claim 9, wherein the therapeutic module controls the driving device further based on another specific image position calculated based on another radiographic image obtained by the other imager at a time when the radiographic image is imaged.

11. The radiation therapy apparatus controller according to claim 7, further comprising a predictable-range calculating module which calculates a predictive range based on a previous specific image position calculated based on a previous radiographic image obtained at a time previous to a time when the radiographic image is imaged, wherein the matching target areas are areas included in the predictive range out of all matching target areas that can be placed in the radiographic image.

12. A radiation therapy apparatus controller for controlling a therapeutic radiation ray irradiation device that irradiates a target subject with a therapeutic radiation ray, the radiation therapy apparatus controller, as part of a computer, comprising:

a storage device having a program stored thereon, wherein the program is executed by the radiation therapy apparatus controller causing the radiation therapy apparatus controller, as part of the computer, to operate as:

a matching module which calculates a plurality of degrees of similarity corresponding to a plurality of matching target areas based on a radiographic image in which the target subject is imaged;

a specific-image position calculating module which calculates a specific image position where a specific image area is positioned in the radiographic image, the specific image area (i) corresponding to a degree of similarity having a maximum value of the plurality of degrees of similarity and (ii) being an area from the plurality of matching target areas; and a radiation therapy module which controls a driving device that drives the therapeutic radiation ray irradiation device that irradiates the target subject with the therapeutic radiation ray based on the calculated specific image position, wherein, when one of the plurality of degrees of similarity corresponding to one of the plurality of matching target areas is calculated by said matching module, said matching module:

refers to a template table in which the matching target areas are associated with a plurality of sets of templates, so as to select, from the plurality of sets of templates, a set of templates corresponding to the one matching target area; and determines, from the selected set of templates, a similar template most similar to a matching target image displayed in the one matching target area of the radiographic image, wherein the one degree of similarity indicates a degree of similarity with which the one matching target area is similar to the similar template, wherein the program is further executed by the radiation therapy apparatus controller causing the radiation therapy apparatus controller to further operate as a template table generating module which generates the template table based on all templates generated from a plurality of template generation radiographic images obtained at a plurality of different times by an imager imaging the radiographic image and a plurality of template positions where all of the generated templates are displayed in the plurality of template generation radiographic images, wherein each of the plurality of template generation radiographic images is divided into a first area and a second area with a straight line passing through one matching target position where the one matching target area is positioned in the radiographic image, wherein the set of templates includes:

a first template, of all of the generated templates, displayed in the first area; and a second template, of all of the generated templates, displayed in the second area, and wherein the straight line passing through the one matching target position is perpendicular to a straight line connecting the first template position and the one matching target position.

* * * * *